US00PP13845P29

(12) United States Plant Patent
Kasai

(10) Patent No.: US PP13,845 P2
(45) Date of Patent: May 27, 2003

(54) *HYDRANGEA ANOMALA* SUBSPECIES PETIOLARIS PLANT NAMED 'KASAI'

(75) Inventor: Seiichi Kasai, Kizukuri-machi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/617,586

(22) Filed: Jul. 18, 2000

(51) Int. Cl.[7] ..... A01H 5/00

(52) U.S. Cl. ..... Plt./250

(58) Field of Search ..... Plt./250

(56) References Cited

U.S. PATENT DOCUMENTS

PP11,038 P * 8/1999 Benarcik, Jr. ..... Plt./250

* cited by examiner

*Primary Examiner*—Kent L. Bell
(74) *Attorney, Agent, or Firm*—Christie, Parker & Hale, LLP

(57) ABSTRACT

A new plant variety of *Hydrangea anomala* subspecies *petiolaris* named 'KASAI' which is characterized by its White variegated foliage. New foliage of 'KASAI' emerges predominantly White with a small amount of Green stippling apparent; as the foliage matures, foliage becomes predominantly Green in color, with some White mottling apparent and White margins; mature foliage is almost entirely Green in color though retaining White variegated margins and occasional White stippling.

4 Drawing Sheets

BACKGROUND OF THE INVENTION

The present invention relates to a new and distinct variety of *Hydrangea anomala* D. Don. subspecies *petiolaris* (Sieb. & Zucc.) McClint., and was discovered as a branch sport in a controlled planting of an unnamed, unpatented *Hydrangea anomala* subspecies *petiolaris* plant in Shinkei-Gun, Aomori City, Aomori Prefecture, Japan, by Mr. Seiichi Kasai. The varietal denomination of the new variety is 'KASAI'.

The genus Hydrangea is included in the family Saxifragacea which comprises about 80 genera and 1,2000 species of herbs, shrubs, small trees and woody climbers mostly temperate in origin. Hydrangea comprises approximately 23 species of deciduous or evergreen shrubs and vines originating in North America, South America and East Asia, many of which possess desirable ornamental characteristics. Recent taxonomical treatments sometimes isolate Hydrangea in a new family, Hydrangeaceae.

*Hydrangea anomala* subspecies *petiolaris* is widespread and common throughout Japan and some locations within Korea. It generally has opposite, oval to rounded leaves 5 to 10 cm long and 3 to 8 cm wide. Leaf apices are acute or acuminate, cordate or round at the base. Leaf margins are serrate, glabrous in surface. The plant is deciduous. Foliage color is dark green on the top surface, and pale green on the underside, depending on light. *Hydrangea anomala* subspecies *petiolaris* differs from *Hydrangea anomala* in having larger leaves and corymbs and a stamen count of 15 to 22, as compared to 9 to 15 stamens found in *Hydrangea anomala*. *Hydrangea anomala* subspecies *petiolaris* has a juvenile and adult phase of growth. Plants in the juvenile growth phase have smaller leaves and do not flower. Some foliar and flowering characteristics change as the plant enters the adult phase. Inflorescences of *Hydrangea anomala* subspecies *petiolaris* bloom June to July, are 15 to 25 cm wide, with the sepals in groups of 3 to 5 on the outer florets. The inner florets are fertile and slightly fragrant.

SUMMARY OF THE INVENTION

The new variety was discovered as a branch sport in a controlled planting of an unnamed, unpatented *Hydrangea anomala* subspecies *petiolaris* plant and differs from its parent in having white foliage variegation. Asexual reproduction of the new variety by stem cuttings performed in Shinkei-Gun, Aomori City, Japan; Lewisberry, Pa.; and Vacaville, Calif. have confirmed that the distinctive characteristics of the new variety are stable and transmitted to succeeding generations, and the new variety reproduces true to type.

COMPARISON WITH PARENT

'KASAI' is distinguished from its parent and all other varieties of *Hydrangea anomala* subspecies *petiolaris* of which I am aware by its white foliage variegation. New foliage of 'KASAI' emerges predominantly white with a small amount of Green stippling apparent; as the foliage matures, foliage becomes predominantly Green in color, with some White mottling apparent and White margins; mature foliage is almost entirely Green in color though retaining White variegated margins and occasional White stippling.

BRIEF DESCRIPTION OF ILLUSTRATIONS

The accompanying photographic illustrations show a specimen of the new cultivar as true to color as is reasonably possible to make in illustrations of this character.

DETAILED DESCRIPTION OF THE NEW VARIETY

Figure 1:
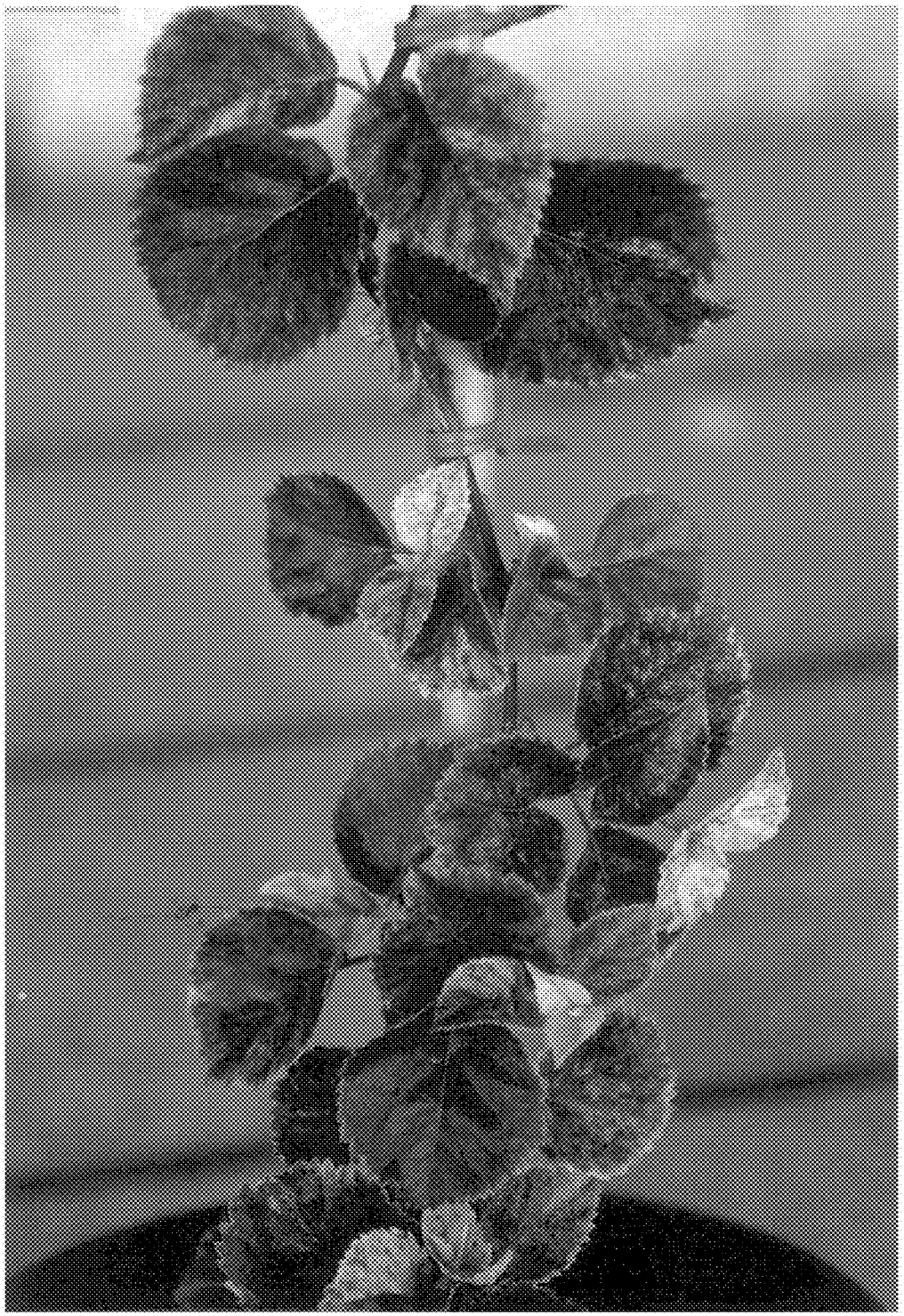
FIG. 1 illustrates the overall plant with new foliage as well as mature foliage.
Figure 2:
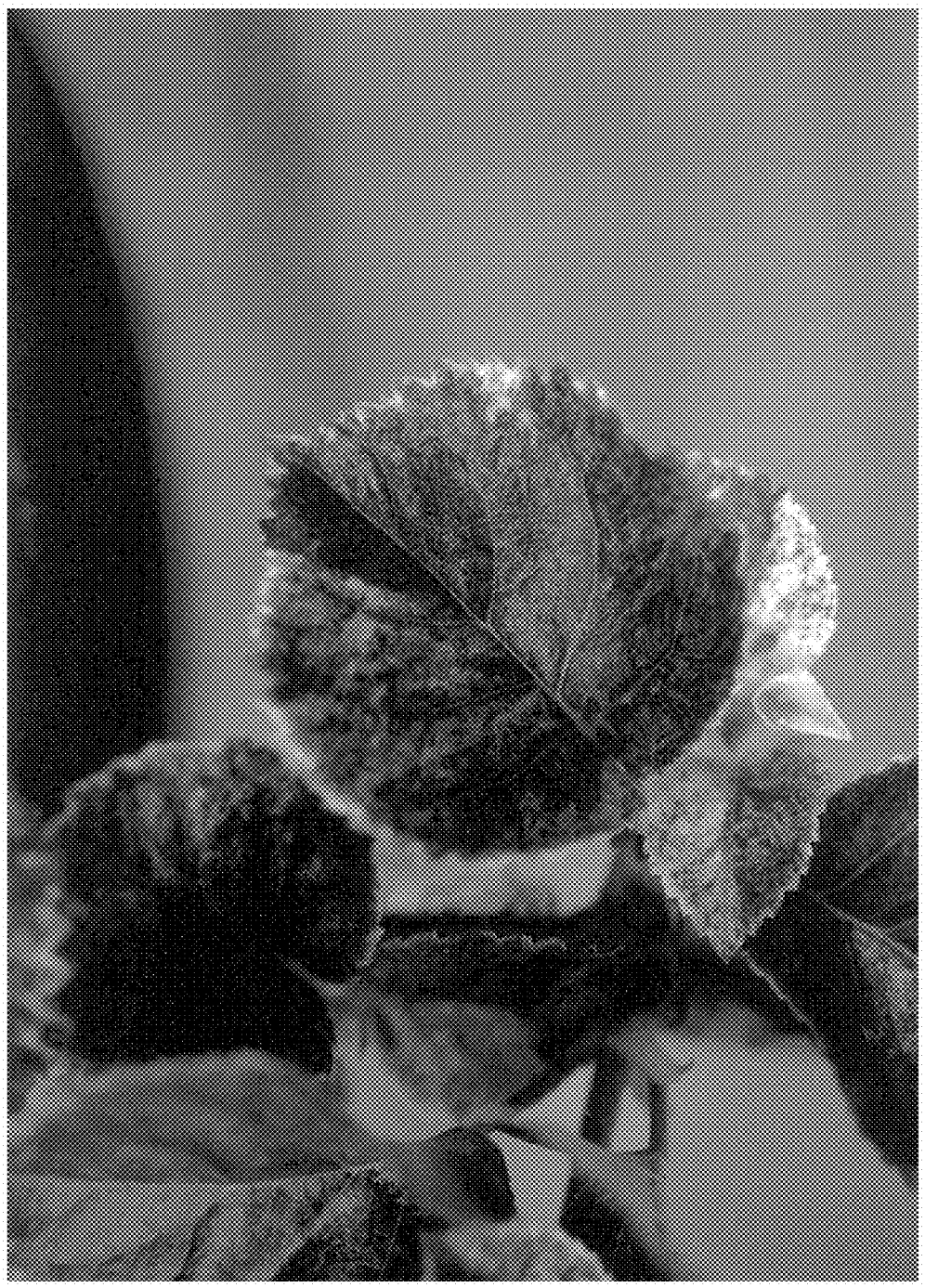
FIG. 2 illustrates the mature foliage with the clear, White variegated margin.
Figure 3:
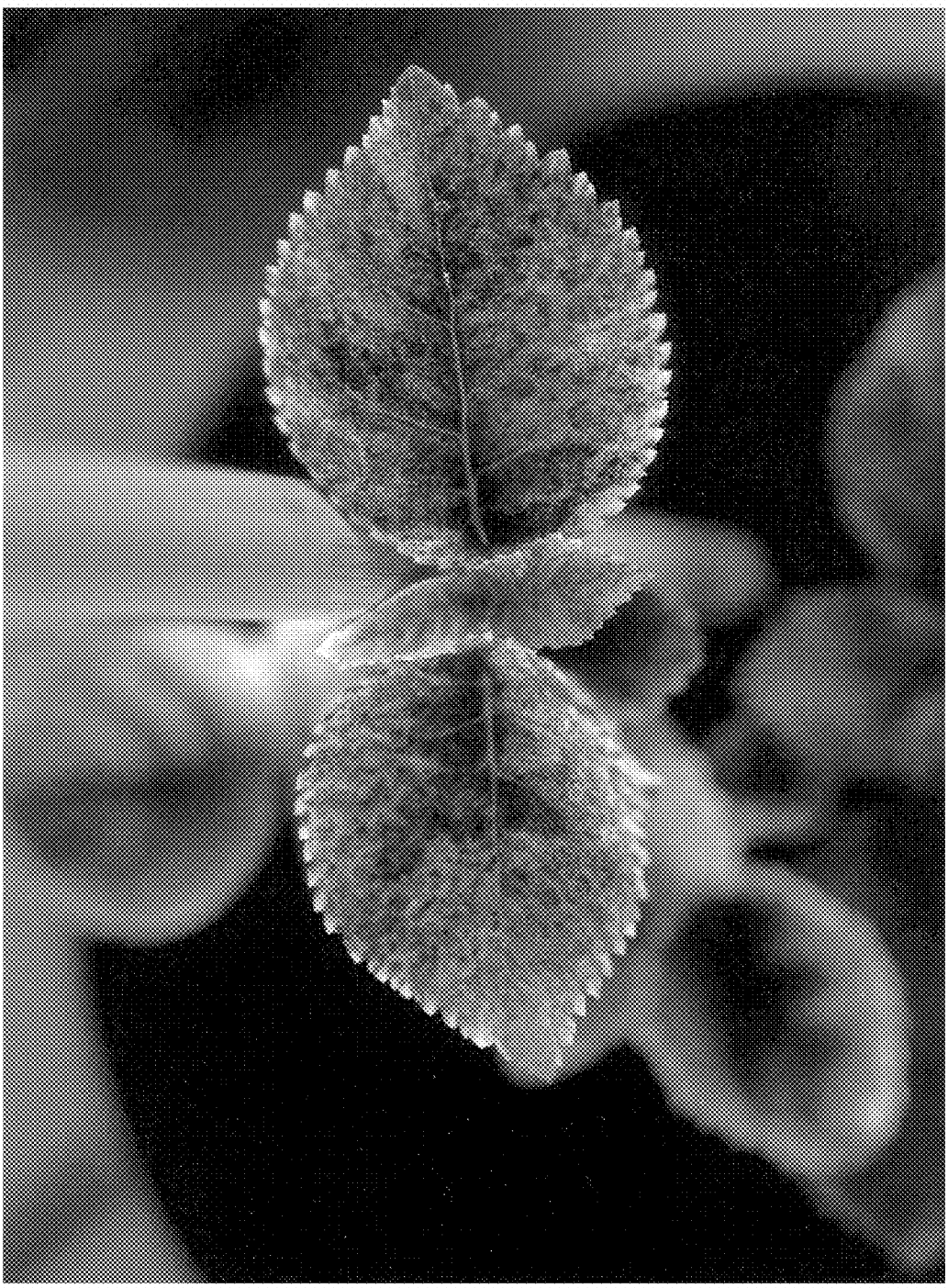
FIG. 3 illustrates the foliage as it is transitioning from new foliage to mature foliage. Note the mottled White foliage variegation.
Figure 4:
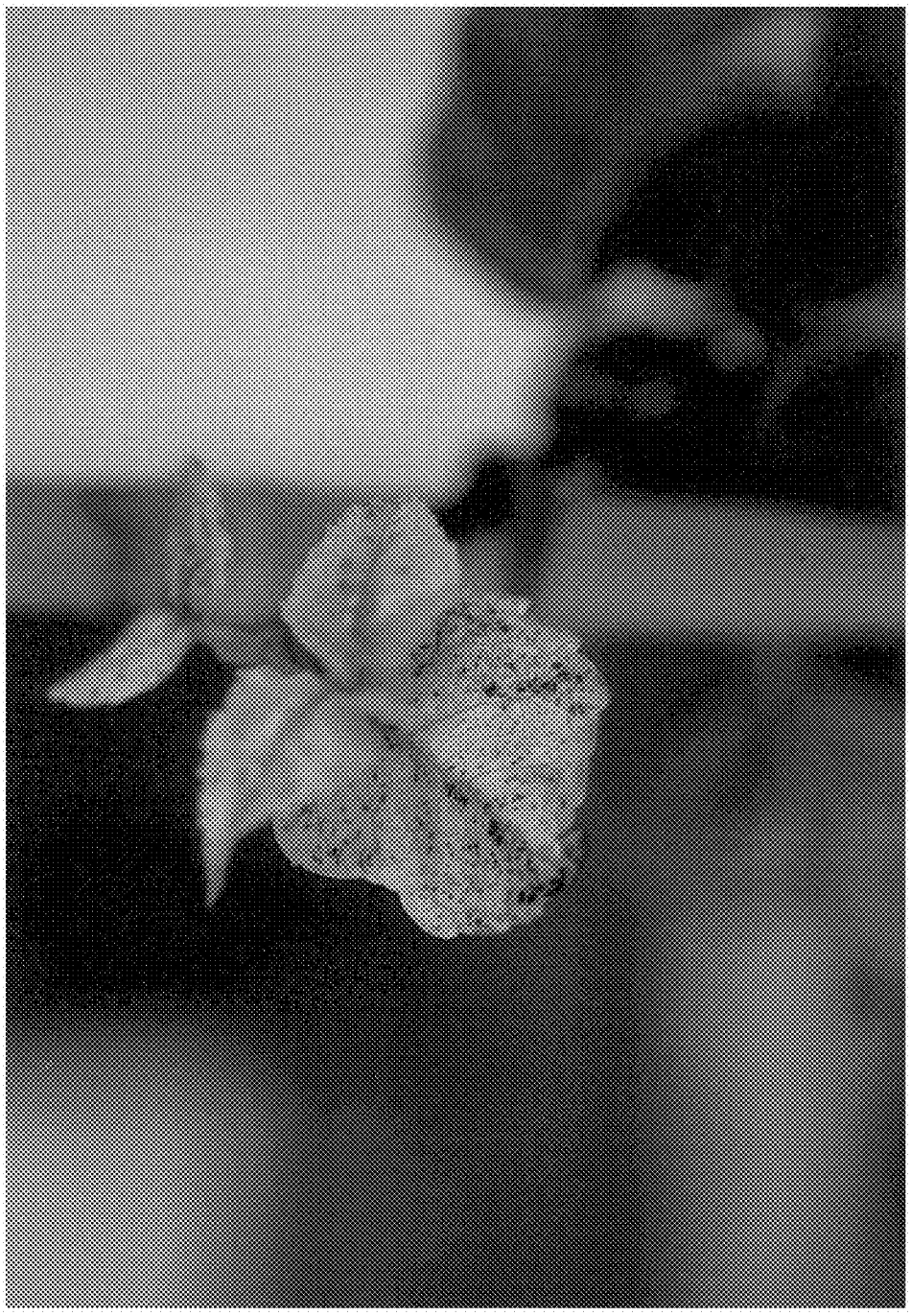
FIG. 4 illustrates the new foliage which is predominately White with some Green stippling.

'KASAI' has not been observed under all possible environmental, cultural, and light conditions. The following observations and descriptions are of 5 year-old plants grown in 10-gallon nursery containers grown in Vacaville, Calif. In this description, color references are to The Royal Horticultural Society Colour Chart (1995) and terminology used in the color descriptions herein refers to plate numbers in this color chart. Phenotypic expression may vary with light intensity, cultural, and environmental conditions.

CLASSIFICATION

Botanical: *Hydrangea anomala* D. Don. subspecies *petiolaris* (Sieb. & Zucc.) McClint. 'KASAI'.
Parentage: Branch sport of a *Hydrangea anomala* subspecies *petiolaris* plant (unnamed, unpatented).
Propagation: By vegetative cuttings.

PLANT

Size: Mature plant can climb and spread to about 16 m at maturity.
Habit: A clinging vine which climbs with root-like holdfasts.
Leaves: Opposite, simple.
Size: Average about 5 cm long and 4 to 5 cm wide.
Leaf shape: Ovate to nearly ovate oval.
*Leaf apex.*—Acute to ovate oval.
*Leaf base.*—Cordate.
*Leaf margin.*—Serrate.
Leaf texture and substance: Firm and glabrous above and below.
Internode length: Average 4 cm.
Stem:
*Texture.*—Hirsute on new growth.
*Color.*—Near Greyed-Orange Group 176B.

COLOR OF LEAVES IN 3 DIFFERENT GROWTH PHASES

New growth: Predominantly White foliage with some Green Stippling.
*Upper side.*—White area near White Group 155B; Green stippling near Green Group 139A.
*Underside.*—White area near White Group 155B; Green stippling near Green Group 139B.
Secondary growth: Predominantly Green foliage with some White mottling on leaf and White marginal variegation.
*Upper side.*—White mottling and marginal variegation near White Group 155B; background near Green Group 139B.
*Underside.*—White mottling and marginal variegation near White Group 155B; background near Green Group 139B.
Mature growth: Almost entirely Green with occasional White stippling and White marginal variegation.
*Upper side.*—White stippling and marginal variegation near White Group 155B; background near Green Group 139A.
*Underside.*—White stippling and marginal variegation near White Group 155B; background near Green Group 139B.
Petioles: Near Yellow-Green Group 145C.
Hardiness: USDA Zone 4 (−30° to −20° F.).
Pests/diseases: No resistance/susceptibility to pests or diseases beyond that of the species has been noted.

INFLORESCENCE

Bloom period: Early to mid-Summer.
Lastingness of individual blooms: To 3 weeks on the plant.
Fragrance: Sweet.
Form: Flat corymbs; 3 to 5 corymbs per plant; outer florets with 3 to 5 sepals; inner florets fertile.
Size: About 15 to 25 cm wide.
Number of flowers per corymb: 10 to 20.
Outer florets: Sepals in groups of 3 to 5, sterile, 5 to 10 cm wide.
Number of sepals per floret: 12 to 18.
Sepal size: 2.5 cm long; 2.5 cm wide.
Sepal shape: Rounded.
Sepal apex: Obtuse.
Sepal base: Attenuate.
Sepal margin: Slightly crenate, occasionally entire.
Sepal color:
*Top.*—Near White Group 155A.
*Bottom.*—Near White Group 155A.
Inner florets: Fertile.
Stamens: 15 to 20.
Pistils: 1.
Fruit: Capsule, dehiscent.

I claim:

1. A new variety of *Hydrangea anomala* subspecies *petiolaris* plant, as illustrated and described.

* * * * *